(12) United States Patent
Gatlin et al.

(10) Patent No.: US 8,951,941 B2
(45) Date of Patent: *Feb. 10, 2015

(54) LOW TEMPERATURE HYDROCARBON GEL II

(75) Inventors: Larry W. Gatlin, San Antonio, TX (US); Glen E. Walden, The Woodlands, TX (US); Ernest McMillan, Kingwood, TX (US); Richard A. Gatlin, Montgomery, TX (US)

(73) Assignee: CST Performance Products Corp., Conroe, TX (US)

( * ) Notice: Subject to any disclaimer, the term of this patent is extended or adjusted under 35 U.S.C. 154(b) by 768 days.

This patent is subject to a terminal disclaimer.

(21) Appl. No.: 13/135,136

(22) Filed: Jun. 27, 2011

(65) Prior Publication Data

US 2012/0000661 A1 Jan. 5, 2012

Related U.S. Application Data

(63) Continuation-in-part of application No. 12/803,683, filed on Jul. 2, 2010, now Pat. No. 8,513,166.

(51) Int. Cl.
| | |
|---|---|
| C09K 8/16 | (2006.01) |
| C09K 8/42 | (2006.01) |
| C09K 8/64 | (2006.01) |
| C23F 11/18 | (2006.01) |
| E21B 43/26 | (2006.01) |
| C09K 8/68 | (2006.01) |
| C07F 15/02 | (2006.01) |

(52) U.S. Cl.
CPC .............. *C07F 15/025* (2013.01); *C09K 8/685* (2013.01); *Y10S 507/923* (2013.01)
USPC ........... 507/109; 507/208; 507/238; 507/271; 507/923; 166/308.1

(58) Field of Classification Search
CPC ............ C09K 8/032; C09K 8/32; C09K 8/52; C09K 8/64; C09K 8/82; Y10S 507/904; Y10S 507/922

USPC ................ 507/109, 208, 271, 922, 923, 238; 166/308.1

See application file for complete search history.

(56) References Cited

U.S. PATENT DOCUMENTS

| | | | |
|---|---|---|---|
| 2,644,828 A | * | 7/1953 | Kruse et al. ............... 556/148 |
| 3,368,627 A | | 2/1968 | Hurst et al. |
| 3,765,488 A | | 10/1973 | Pence, Jr. |
| 3,842,910 A | | 10/1974 | Zingg et al. |
| 3,846,310 A | | 11/1974 | Blackwell et al. |
| 3,954,626 A | | 5/1976 | Greninger, Jr. et al. |
| 4,877,894 A | | 10/1989 | Huddleston |
| 4,964,467 A | | 10/1990 | Holtmyer et al. |
| 5,110,485 A | | 5/1992 | Huddleston |
| 5,417,287 A | | 5/1995 | Smith et al. |
| 5,571,315 A | | 11/1996 | Smith et al. |
| 5,614,010 A | | 3/1997 | Smith et al. |
| 5,647,900 A | | 7/1997 | Smith et al. |
| 5,807,812 A | | 9/1998 | Smith et al. |
| 5,899,272 A | | 5/1999 | Loree |
| 5,948,735 A | | 9/1999 | Newlove et al. |
| 6,054,417 A | | 4/2000 | Graham et al. |
| 6,147,034 A | | 11/2000 | Jones et al. |
| 6,342,468 B1 | | 1/2002 | Geib |
| 6,719,053 B2 | | 4/2004 | Thompson |
| 7,163,060 B2 | | 1/2007 | Weiss et al. |
| 7,328,744 B2 | | 2/2008 | Taylor et al. |
| 7,341,103 B2 | | 3/2008 | Taylor |
| 7,622,054 B2 | | 11/2009 | Delgado et al. |

* cited by examiner

*Primary Examiner* — Aiqun Li
(74) *Attorney, Agent, or Firm* — Beck & Thomas, P.C.

(57) ABSTRACT

A composition useful for crosslinking phosphate esters in hydrocarbon gels used in formation fracturing performs especially well in cold temperatures, such as temperatures lower than (−)20° C. Methods of making the crosslinking composition and the gel are described; also methods of fracturing subterranean formations. Specific forms of ferric sulfate and ferric ammonium citrate are useful as ingredients of the crosslinking composition.

10 Claims, No Drawings

LOW TEMPERATURE HYDROCARBON GEL II

RELATED APPLICATION

This is a continuation-in-part of application Ser. No. 12/803,683 filed Jul. 2, 2010 now U.S. Pat. No. 8,513,166 which is specifically incorporated herein in its entirety, and for which the full benefit thereof is claimed.

TECHNICAL FIELD

Compositions and methods of making liquefied propane gas ("LPG") gels are disclosed; they are useful in formation fracturing for hydrocarbon recovery under extreme cold conditions. A particular iron-containing crosslinking composition including ferric ammonium citrate is mixed and combined with phosphate esters made with low molecular weight alcohols for inclusion with the LPG.

BACKGROUND OF THE INVENTION

Gelled hydrocarbon fluids have been used for pipeline cleaning, well stimulation, and for cleaning well bores, but the most common and economically important use for gelled fluids in hydrocarbon recovery is in formation fracturing, which is well known. See, for example, Smith et al U.S. Pat. No. 5,417,287, Graham et al U.S. Pat. No. 6,004,908 and U.S. Pat. No. 6,147,034, and Taylor et al U.S. Pat. Nos. 6,511,944, 6,544,934, and U.S. Pat. No. 7,341,103. The gelled liquid is sent down the well under great pressure and through perforations in the well piping, where it causes fractures in the earth formation. The gelled fluid typically will also suspend and transport a hard granular material such as sand, known as a "proppant" for its function of maintaining the openings of the fissures so the recovered oil or gas can be drawn from the formation into the recovery system. The gelled fracturing fluid will typically also carry with it compatible gel breakers, as the operators will not want the gel to impede the flow of indigenous hydrocarbons once the proppants are in place.

Generally, the hydrocarbon gels comprise a hydrocarbon base such as an oil, a phosphate ester or phosphonic acid ester, and an aluminum or iron salt as a crosslinker. In addition to forming a gel by crosslinking, the phosphate ester component functions as a corrosion inhibitor for the tubes, pipes and metal apparatus used in drilling, and the iron compounds can function as sulfide scavengers especially in the presence of oxygen.

While the hydrocarbon base is conventionally kerosene, diesel oil, fuel oils, gas distillates, crude oil, and even esters or olefins, it has not been until recently that liquefied petroleum gas, sometimes known as LPG, has been used for the hydrocarbon base. Commercial LPG commonly contains about 90% propane, but the composition may vary somewhat. LPG is used as the base hydrocarbon, or for mixing with a base hydrocarbon, by Taylor et al in U.S. Pat. No. 7,341,103.

As related in Fordyce et al U.S. patent application Ser. No. 12/345,531, paragraph 0030:

"LPG's tend to produce excellent fracturing fluids. LPG is readily available, cost effective and is easily and safely handled on surface as a liquid under moderate pressure. LPG is completely compatible with formations and formation fluids, is highly soluble in formation hydrocarbons and eliminates phase trapping—resulting in increased well production. LPG may be readily and predictably viscosified to generate a fluid capable of efficient fracture creation and excellent proppant transport. After fracturing, LPG may be recovered very rapidly, allowing savings on cleanup costs."

While Fordyce et al say that LPG can be readily and predictably viscosified, they do not describe gel generating compositions for LPG to be used in extreme low temperatures. See also Loree et al U.S. patent application Ser. No. 12/203,072, paragraph 0042:

". . . the extremely low surface tension of the LPG eliminates or at least significantly reduces the formation of liquid blocks created by fluid trapping in the pores of the formation. This is contrasted with the high surface tension of water, which makes water less desirable as a conventional fluid. LPG is nearly half the density of water, and generates gas at approximately 272 $m^{(3)}$ gas/$m^{(3)}$ of liquid. LPG comprising butane and propane has a hydrostatic gradient at 5.1 kPa/m, which greatly assists any post-treatment clean-up required, by allowing greater drawdown. This hydrostatic head is approximately half the hydrostatic head of water, indicating that LPG is a naturally under balanced fluid.

Again, while Loree et al describe apparatus and methods said to overcome the difficulties incident to the incorporation of proppant into LPG fracturing fluids, they do not address the chemistry of gels useful for LPG or propane fracturing fluids in extreme low temperatures—that is, −20° C. or lower.

Workers in the art have had difficulties making functional LPG gels, utilizing prior art gelling methods and ingredients, under very cold conditions at the wellhead where the temperature may be −20° C. or lower. Under such conditions, conventional gel systems react only sluggishly and tend to be too viscous.

SUMMARY OF THE INVENTION

We have invented a hydrocarbon gel, a method of making it, and a method of fracturing the earth all of which overcome the difficulties that extreme low temperatures impose on conventional gels, including gels using LPG as a base hydrocarbon. Our gel system achieves a useful viscosity within an appropriately short period. Our gels are able also to carry a range of types of proppants and other materials, and are amenable to the use of gel breakers.

The hydrocarbon base for our extreme low temperature gel is propane. More particularly, we may use liquefied propane or mixtures of low molecular weight alkanes having from one to four carbon atoms, the mixture including at least 85% propane. As is known in the art, commercial liquefied petroleum gas (LPG) may be found having various ranges of content of methane, ethane, propane, butane, isobutene, and pentane.

Our hydrocarbon base should not contain more than two percent pentane. Such liquefied gas mixtures of $C_{1-4}$ alkanes, of which at least 85% by weight is propane, and containing no more than 2% pentane, are hereinafter called liquefied propane, or LPG. Of course this definition includes a liquefied gas which is substantially entirely propane, and the lower alkanes recited herein may come from any source.

Liquefied propane is gelled at extreme low temperatures in our invention with the use of a unique crosslinking system designed for extreme low temperatures. The crosslinking (gel forming) system has two components—a phosphoric acid ester, and a ferric iron source. Each of these has particular defined elements. The gelled liquefied propane may be mixed with a conventional hydrocarbon fracturing fluid if desired.

The phosphate ester component we use is a $C_{3-6}$ alkanol phosphate diester, as will be described below. We have further found that phosphate diesters made from significant portions of low molecular weight trialkane phosphates, specifically trimethyl phosphate and triethyl phosphate, may be used to excellent effect in gelling LPG at very low temperatures, provided our novel crosslinker is employed with them.

The ferric iron source may be the reaction product of (a) ferric sulfate, (b) ferric ammonium citrate (red or brown), (c) citric acid, (d) ammonium hydroxide, and (e) monoisopropanolamine, in the proportions and according to the procedure described elsewhere herein, in the presence of glycerin, sodium cumene sulfonate, unavoidable water, and, optionally, sorbitol. In accordance with the findings presented in this continuation-in-part patent application, we are able to achieve excellent results at very low temperatures without using either glycerin or sorbitol, to make the iron-containing crosslinker.

The two basic components, the phosphate ester and the iron-containing crosslinker, are brought together with the LPG (and additional hydrocarbon fluid, if any, proppant, and other possible additives) at the wellhead before pumping the mixture down the well in a fracturing or other process.

DETAILED DESCRIPTION OF THE INVENTION

Our invention will be described in the following particulars.

Typical Preparation of the Ferric Iron Source Component ("Crosslinker")

To an appropriate reactor, ingredients are added for alternative Formulas A or B:

|  | Formula A | Formula B |
| --- | --- | --- |
| 60% ferric sulfate | 45.97% by weight | 48.95% by wt |
| Citric acid, 100% | 9.14% | 9.73% |
| Monoisopropanolamine (MIPA) | 8.14% | 8.67% |
| Ammonium Hydroxide, 30% (26BE) | 9.71% | 10.34% |
| Ferric Ammonium Citrate (brown) | 3.50% | 3.73% |
| Sodium Cumene Sulfonate, 40% | 9.50% | 10.11% |
| Glycerin, USP | 7.96% | 8.47% |
| Sorbitol, 70% | 6.08% | — |
|  | 100.00% by wt | 100.00% by wt |

Formula B has no sorbitol; the other ingredients have been adjusted in the same proportions to each other as in Formula A, to make 100%.

(1) Place the ferric sulfate in the reactor, (2) add the (powdered) citric acid and the (3) MIPA; then (4) add the aqua ammonia and mix until uniform and homogeneous; then (5) slowly add the ferric ammonium citrate, assuring dissolution as the addition proceeds, then (6) the sodium cumene sulfonate; (7) then add the glycerin, then (8) the sorbitol (optional). The reaction is exothermic.

The ferric sulfate we use contains about 1% sulfuric acid. This form of ferric sulfate is available commercially, as is a form which has about 0.1% sulfuric acid. For our purposes, the ferric sulfate should contain from 0.8% by weight to 1.5% by weight sulfuric acid. A commercial ferric sulfate we have found quite useful contains 60% ferric sulfate, 1% sulfuric acid, and 39% water, but of course the ratio of water to ferric sulfate may vary somewhat within the scope of our invention. It may be said that the sulfuric acid may vary from 1.3% to 2.16% of the ferric sulfate, with the balance water to make 100% by weight. During the reaction, the ferric sulfate containing sulfuric acid reacts with ammonia from the ammonium hydroxide, forming ammonium sulfate.

During the process also, an amine citrate is formed by the reaction of citric acid with the monoisopropanolamine; ferric ammonium citrate is also created in situ. This is the reaction for which the sulfuric acid-containing ferric sulfate appears to be necessary; also it has been demonstrated that the reaction is much enhanced by the presence in the reaction mixture of the red or brown ferric ammonium citrate. Aiding the reaction is ammoniation of the sodium cumene sulfonate, which also occurs.

The combined reaction is exothermic, generally achieving a temperature of about 160-170° F., although other temperatures may be seen depending on the particular procedure and equipment used. Permit the product to cool to ambient temperature; it can be placed in plastic totes or polymeric drums for shipment.

It is known that ferric ammonium citrate occurs commonly, or at least commercially, in a red form, a brown form, and a green form. The green form generally contains about 14.5-16% iron, about 7.5% $NH_3$, and about 75% hydrated citric acid. The red and brown forms generally contain 16.5-18.5% iron, about 9% $NH_3$, and about 65% hydrated citric acid. We have found it necessary to use the red or brown form in our invention in order to make the facilitating amount of ferric ammonium citrate under the extreme cold and pressurized conditions of gel formation during its use. Thus the ferric ammonium citrate ingredient in our formulation is known herein as the red or brown ferric ammonium citrate or ferric ammonium citrate containing 16.5-18.5% iron. We may refer to this ingredient, containing 16.5-18.5% iron by weight, as "red or brown FAC" or "red or brown ferric ammonium citrate," or ferric ammonium citrate (red or brown)." While green FAC is functional at temperatures of 15-35° C., we have found that only our formula containing red or brown FAC will form a gel in liquefied propane. The same formula substituting green FAC is not reliable.

It should be understood that the percentages and relative proportions of the above listing of ingredients in "Typical formulations" A and B may vary. Generally, our invention is operable when any given ingredient in the above lists is varied plus or minus 5%, with the percentages of the others being adjusted so as to total 100%. Some ingredients may be increased 5% while others are reduced 5%. An exception is sorbitol, which of course can be completely eliminated in Formula A.

The sorbitol and glycerin in the above typical formulas function to ameliorate possible negative effects on the gel of the unavoidable amount of water in the formulation. Their hygroscopic properties tend to discourage water from contacting the crosslinked complex. As they are not reactants for the crosslinking and gelling functions, their proportionate amounts may vary somewhat more than other components of the formulation. Indeed, as indicated above, we have found that the sorbitol is not necessary at all, and accordingly, not only can the sorbitol be completely eliminated, but the glycerin can vary more in its proportion than the other ingredients when the sorbitol is not included. Also, the sodium cumene sulfonate (SCS) does not enter into the chemical reaction—it is a hydrotrope employed to maintain the reactants in a clear solution and to prevent separation; however, although not essential, the SCS is recommended (sodium xylene sulfonate may be substituted), since its partial ammoniation also appears to aid in the formation of ferric ammonium citrate. Nevertheless, a more or less idealized listing of reactants for the typical formula may be restated:

| | Formula C (Reactants) |
|---|---|
| 60% ferric sulfate | 60.1% by weight |
| Citric acid, 100% | 12% |
| Sorbitol, 70% | — |
| Glycerin, USP | — |
| Monoisopropanolamine (MIPA) | 10.6% |
| Ammonium Hydroxide, 30% (26BE) | 12.7% |
| Sodium Cumene Sulfonate, 40% | — |
| Ferric Ammonium Citrate (brown) | 4.6% |
| | 100.00% |

Again, as indicated above, the amount of each of the reactants listed in Formula C can readily vary as much as 5% more or less of its own content, with the other ingredients being adjusted accordingly to maintain ratios to each other appropriate to total 100%. Therefore it will be understood that, while more than one ingredient may be increased or decreased, more or less than five percent of the above stated portions may lead to wasteful or undesirable excesses of one or more inunreacted ingredients mixed in the final product. If compatible substitutes are found for the sorbitol, glycerin, and SCS which are able to perform the above stated functions for them, they may be used.

Also it should be noted that there are significant amounts of water in the ferric sulfate and the ammonium hydroxide and that the water content of these and possible minor amounts in the other ingredients (including especially the SCS). Water is generally not desirable in the final product, which is designed for use in hydrocarbon bases, and accordingly reactants that have more water than the stated amounts in Formula C (such as the 40% in ferric sulfate and 70% in the ammonium hydroxide) are not recommended. But it should be noted that Formula A includes about 41.8% water from various sources, and since it may be possible to vary the amounts of water from more than one source, the reactants of Formula C may be restated in terms of non-aqueous reactants, as follows:

| | |
|---|---|
| 60% ferric sulfate | 53.7% by weight |
| Citric acid, 100% | 17.9% by weight |
| Monoisopropanolamine (MIPA) | 15.8% by weight |
| Ammonium Hydroxide, 30% (26BE) | 5.7% by weight |
| FAC (red or brown) | 6.9% by weight |
| | 100.0% |

Keeping the above in mind, it will nevertheless be understood that the Formula C reactants, including their respective water contents, may be restated in terms of parts by weight of their normal water-containing components which do not need to add up to 100:

| Formula C Reactants in Parts by Weight | |
|---|---|
| 60% ferric sulfate | 57 to 63.5 parts by weight |
| Citric acid, 100% | 11.4 to 12.6 parts by weight |
| Monoisopropanolamine (MIPA) | 10.07 to 11.13 parts by weight |
| Ammonium Hydroxide, 30% (26BE) | 12.06 to 13.33 parts by weight |
| FAC (red or brown) | 4.37 to 4.83 parts by weight |

However, we do not intend to be limited to these particular limits or ratios, as workers skilled in the art of chemistry may adjust the conditions of the reaction to achieve satisfactory results. Moreover, it should be understood that the ingredients will participate in the reaction in the appropriate ratios to each other indicated in the above list of "Formula C Reactants in Parts by Weight," regardless of an excess or deficit of one or more of them. For example, if there are present 15 parts by weight citric acid, the excess 2.4 parts do not prevent the reaction from reacting in the appropriate ratios; an excess of unreacted citric acid mixed with the reaction product will not inhibit the overall reaction—the citric acid actually present will react roughly in the ratios to the other ingredients indicated, possibly leaving portions of other ingredients unreacted. Likewise, in any of our expressions of our formulas there can be a significant excess of ferric sulfate (as much as 40% or more in excess, for example); modest excesses may be advantageous in some circumstances. In other words, our new composition is the product of the reaction of the ingredients of "Formula C Reactants" whether or not excess unreacted components of the reaction mixture are present with them.

Glycerin is desirably also included in an amount effective to inhibit the water necessarily present in the mixture from contacting the resulting iron crosslinker. In the above "Formula C Reactants in Parts by Weight," a beneficial amount of glycerin would be 7 to 14 additional parts by weight, but higher or lower amounts may accomplish the desired results.

A useful formula for our crosslinker specific to this continuation-in-part application may be referred to as Formula D:

| Formula D | Weight Percent | Active Wt. Percent |
|---|---|---|
| 60% ferric sulfate | 53.31 | 32 |
| Citric acid, 100% | 10.60 | 10.6 |
| Monoisopropanolamine (MIPA) | 9.44 | 9.44 |
| Ammonium Hydroxide, 29.4% (26Be) | 11.26 | 3.31 |
| Sodium Cumene Sulfonate, 40% | 11.33 | 4.53 |
| FAC (red or brown) | 4.06 | 4.06 |
| | 100.00 | 63.94 |

Although these ingredients add up to 100%, it should be understood as with the other formulations above that the active weight percent of each of the ingredients may be varied in concentration by plus or minus 5%, with the other ingredients being adjusted accordingly to be maintained within ±5% of their recited concentrations. An exception, however, is citric acid. Citric acid may be present in an amount from 10 to 50 parts by weight, as is indicated in the following "Formula D Distended"

| Formula D Distended | Parts by weight | Active parts by weight |
|---|---|---|
| 60% ferric sulfate | 50 to 56 | 30 to 33.6 |
| Citric acid, 100% | 10 to 50 | |
| Monoisopropanolamine (MIPA) | 8.9 to 10 | |
| Ammonium Hydroxide, 29.4% (26Be) | 10.6 to 12 | 3.1 to 3.6 |
| Sodium Cumene Sulfonate, 40% | 10.7 to 12 | 4.25 to 4.8 |
| Ferric Ammonium Citrate (red or brown) | 3.8 to 4.5 | |

Note that as much as 50 parts by weight citric acid may be included. Glycerine could be added to Formula D Distended in an amount within the discretion of the formulator, for its hygroscopic effects. Note also that the ferric sulfate, ammonium hydroxide, and SCS allow for about 40%, 70.6%, and 60% water respectively. If more or less water is included in any of these or any of the other ingredients of Formula D Distended, the concentration equivalent should be calculated from the Formula D Distended table. In any of our crosslinker formulations, any unstated amounts of water (more or less than stated) in each ingredient may be ignored in calculating said parts by weight. Regardless of the amount of water in any of our crosslinking formulations, it is advantageous in the very cold conditions for which they are designed to remove substantially all the water from the fully reacted product, yielding a dry product not subject to freezing. Accordingly, where a dry product is to be made, a minimum amount of water in the reaction mixture is preferred. Water may be removed from the reaction product by evaporation, for example.

Typical Preparation of the Phosphate Ester

The reader may wish to compare the following manufacture of phosphate diesters with the examples of Huddleston in U.S. Pat. No. 4,877,894 and U.S. Pat. No. 5,110,485, which utilize higher molecular weight alcohols.

Two moles of triethyl phosphate $O=P(OC_2H_5)_3$ are reacted in an inert atmosphere (nitrogen; less than 2% oxygen) with one or more moles of phosphoric acid $P_2O_5$ (sometimes expressed $P_4O_{10}$) by maintaining the mixture at about 248° F. for about three hours to make a polyphosphate product, which is then reacted at 185° F. in turn with two moles each of lower alkanols such as hexanol, pentanol, butanol, propanol and/or ethanol; separate additions can be made in sequence. Isopropanol may be substituted for the n-propanol, and the hydroxyl groups may appear anywhere in the other small chain alcohols. Branching is beneficial in that improved hydrocarbon solubility may be expected. Addition of the alcohols may be varied and/or changed in sequence. Some heat removal will be required; temperature may be reduced to about 185° F. The acid number of the product should be at least 200; in any event, the acid number can be increased by adding $P_2O_5$ This recipe will make 4,5,6 diesters. However, note that formulas A, B, and C below employ no alcohols higher than butanol. Products of the process described in this paragraph having the ingredients of Formulas A, B, and C in the table of "Phosphate Variants" shown below may be referred to herein as C3-C4 Phosphate Diesters or $C_3$ and $C_4$ alkanol phosphate diesters. Trimethyl phosphate may be substituted for triethyl phosphate.

Other phosphate esters useful in our invention may be made by following the general procedure outlined above, using the ingredients seen in the following table titled Phosphate Variants, in which the term TEP is triethylene phosphate, C3 is propanol, C4 is butanol, C5 is pentanol, and C6 is hexanol; numbers in the table are moles:

| | Phosphate Variants | | | | | |
|---|---|---|---|---|---|---|
| | | | Example | | | |
| | A<br>C4 | B<br>C3 | C<br>C3/4 | D<br>C5/6 | E<br>C5/6(3:1) | F<br>C4/5/6 |
| TEP | 2 | 2 | 2 | 2 | 2 | 2 |
| P2O5 | 1 | 1 | 1 | 1 | 1 | 1 |
| n-C3OH | — | 6 | 3 | — | — | — |
| n-C4OH | 6 | — | 3 | — | — | 2 |
| n-C5OH | — | — | — | 3 | 4.5 | 2 |
| n-C6OH | — | — | — | 3 | 1.0 | 2 |

As indicated above, ethanol may also be used, either by itself of in mixture with other alcohols having up to 6 carbon atoms. Generally, the phosphate esters we may use are the reaction products of two moles of tri(lower alkyl) phosphates of the formula $O=P(OC_xH_{2x+1})_3$ where x is 1-5 with phosphoric acid (1.0 to 1.5 moles) to achieve a polyphosphate which is then reacted with six moles of one or more lower alcohols. C6 alcohols are not preferred, however. Excellent gels are made using our crosslinker with a phosphate ester where x is 2 and the alcohols are alcohols having from 2 to 5 carbons. Thus the phosphate esters we use may be defined as diesters of alcohols having 2 to 5 carbon atoms with an amine polyphosphate which is a reaction product of a trialkyl phosphate, typically of the formula $O=P(OC_2H_5)_3$, with phosphoric acid. Typical reaction yield is, by weight: diester, >72.1%, monoester ~9%, inorganic $PO_4$<1%, free alcohol ~19%.

Gel Tests

Gel formation was tested using Phosphate Variant F for seven iron crosslinker formulations made of the ingredients shown in Table 1:

Iron crosslinker formulations were made of the ingredients shown in Table 1.

TABLE 1

| Form-<br>ula | 60%<br>Ferric<br>Sul-<br>fate[1] | 100%<br>Citric<br>Acid | 100%<br>MIPA[2] | 28%<br>Aqua<br>NH[3] | 100%<br>Gly-<br>Cerin | 70%<br>Sor-<br>Bitol | FAC[3] | SCS[4] | Total<br>Equiv-<br>alent[5] |
|---|---|---|---|---|---|---|---|---|---|
| A | 45.97 | 9.14 | 8.14 | 9.71 | 7.96 | 6.08 | 3.50 | 9.50 | 100 |
| B | 45.97 | 9.14 | 8.14 | 9.71 | 7.96 | — | 3.50 | 9.50 | 93.92 |
| C | 45.97 | 9.14 | 8.14 | 9.71 | — | 6.08 | 3.50 | 9.50 | 92.04 |
| D | 45.97 | 9.14 | 8.14 | 9.71 | — | — | 3.50 | 9.50 | 85.96 |
| E | 45.97 | 9.14 | 8.14 | 9.71 | 7.96 | 6.08 | 3.50 | — | 90.50 |
| F | 45.97 | 9.14 | 8.14 | 9.71 | 7.96 | 6.08 | — | 9.50 | 96.50 |
| G | 45.97 | 9.14 | 8.14 | 9.71 | — | — | —[6] | — | 72.96 |

[1]The ferric sulfate contained 1.0% sulfuric acid.
[2]MIPA is monoisopropanolamine.
[3]FAC is brown ferric ammonium chloride.
[4]SCS is sodium cumene sulfonate.
[5]Unlike the expressions of Formulas A and B above, these compositions have not been adjusted to total 100%.
[6]Although ferric ammonium citrate is manufactured in the process, this composition without any FAC originally in the reactor yields poor gel results-see below.

All formulations A-G make stable solutions in pentane at (−)29° C.

Formulations A-G were also tested with Phosphate Variant F at 20 degrees above zero Centigrade, with the results shown in Table 2:

TABLE 2

| Crosslinker | Vc (minutes)[2] | C (minutes)[3] | Appearance[4] |
|---|---|---|---|
| Commercial[1] | 17 | 31 | Rigid |
| A | 16 | 40 | very rigid |
| B | 8 | 13 | rigid and tight |
| C | 49 | 1:08 | poor yield/gel |
| D | 12 | 32 | very rigid |
| E | 29 | — | Incompletely gelled |
| F | 11 | 23 | poor yield/gel |
| G | 29 | 41 | poor yield |
| A (green FAC) | 11 | 29 | Rigid and tight |

[1]A readily available commercial gelling agent.
[2]Vc is "closure." See the discussion below.
[3]C is "crown." See the discussion below.
[4]These are more or less subjective observations. In order of quality and desirability, from best to least effective: very rigid, rigid and tight, rigid. Poor yield/gel means generally consolidated but insufficiently gelled.

The gel test employs a standard Hamilton Beach mixer at a controlled moderate speed. Liquid pentane or propane is the base hydrocarbon liquid; where the test is conducted at room temperature or 20° C., the temperature will drop somewhat because of the temperature of the liquid base; this is not measured. The timer is started immediately on addition of the last ingredient, and the mix will be expected immediately to exhibit a vortex. As the viscosity continues to build, the vortex will recede. When a vortex is no longer visible, the time, in minutes, is recorded as "closure," noted as "Vc." Mixing continues, and the fluid builds a slight mound, called the "crown," the time, in minutes, for which is recorded as "C." Sometimes in the very cold conditions the crown will occur before the closure.

Example 1

In this demonstration, a gel system consisting of 1.5 milliliters Phosphate Variant F and 1 ml of a commercial hard burned Magnesium oxide gel breaker were suspended in oil and 2.5 mls of crosslinker Formula A were subjected to the gel test in liquid pentane at 29° C. below 0, resulting in a crown in 8 minutes 25 seconds, and yielding a lippy gel (very good; rigid) Equal amounts of a commercial phosphate ester, MgO gel breaker and commercial iron crosslinker at −29° C. yielded no close or crown in more than 15 minutes. Our gel system is clearly superior at these low temperatures.

Example 2

In order to demonstrate the effect of the sulfuric acid in the ferric sulfate, gel tests were performed. The gel agent in each case was Phosphate Variant F. In each case, 1.5 mls of the phosphate gel agent was added to 250 mls of pentane and 1 ml of hardburned magnesium oxide gel breaker was added. 1.5 milliliters of crosslinker made according to Formula A in Table 1 was also added, except that in Sample 1, sulfuric acid in the ferric sulfate was less than 1% by weight. For Sample 2, 1% sulfuric acid was added to the ferric sulfate used in Sample 1, and in Sample 3, 2% sulfuric acid was added to the ferric sulfate used in Sample 1. The gel tests were conducted at room temperature and at (−)20° C. Results were as follows:

| Room Temperature (20-25° C.) | | |
|---|---|---|
| Sample 1: | Vc = 10 seconds | C = 22 seconds |
| Sample 2: | Vc = 9 seconds | C = 20 seconds |
| Sample 3: | Vc = 10 seconds | C = 29 seconds |

| Cold Temperature (20 to 29 degrees below zero C.) | | |
|---|---|---|
| | Vc | C |
| Sample 1 | 45 seconds; Keeps reopening | 2:05 minutes; Reopened |
| Sample 2 | 34 seconds | 1:05 to 1:32 minutes; Closes early |
| Sample 3 | 55 seconds; Slow to close | 1:50 minutes |

Sample 2, made with ferric sulfate containing 1% added sulfuric acid, is clearly the best performer at cold temperatures. Ineffective Sample 1 used ferric sulfate described by the manufacturer as including "<1% sulfuric acid." Ineffective Sample 3 is the same as Sample 1 except that the ferric sulfate contained an additional 2% sulfuric acid. Our invention, demonstrated by Sample 2, therefore employs ferric sulfate containing from 0.8 to 1.5% sulfuric acid.

Example 3

Here, three combinations were compared for gel formation at (−)29° C., using the same relative amounts as Example 1:

First, 1.5 mls Phosphate Variant F, 1 ml of a commercial MgO gel breaker suspended in oil and 2.5 mls of crosslinker Formula B were subjected to the gel test in pentane at (−)29° C., resulting in Vc=1 min 18 secs and C=2 min 25 secs.

Second, 1 ml Phosphate Variant F, 1 ml of a commercial MgO gel breaker suspended in oil and 1.5 mls of crosslinker Formula B were subjected to the gel test in pentane at (−)29° C., resulting in Vc=1 and C=6 minutes 4 seconds, yielding a rigid gel.

Third, 1.5 mls phosphate variant F, 1 ml of a commercial MgO gel breaker suspended in oil and 2.5 mls of crosslinker Formula A with the brown FAC substituted by green FAC were subjected to the gel test in pentane at (−)29° C., resulting in Vc=1 min 18 secs and C=2 min 25 secs, resulting in no close or crown in 6 minutes; a slush only was obtained with no rigid gel.

Example 3 clearly demonstrates that the brown FAC must be used rather than the green FAC, reinforcing the finding of Example 2.

Example 4

Four tests were run to compare the efficacy of our formulations containing gel breakers. The compositions and their viscosity test (gel formation at 20° and break test at 55° C.) results were as follows:

| | Comp. 1 | Comp. 2 | Comp. 3 | Comp. 4 |
|---|---|---|---|---|
| Phosphate Gellant | Variant F 1.5 mls | Variant F 1.5 mls | Variant F 1.5 mls | Variant F 1.5 ml |
| Breaker (hard burned Mg) | Brand A 1 ml | Brand B 1 ml | Brand B 1 ml | Brand A 1 ml |
| Xlinker | Formula A[5] 1.5 ml | Formula A[5] 1.5 ml | Formula B[2] 1.5 ml | Formula B[2] 1.5 ml |
| Vc | 14 seconds | 16 seconds | 9 seconds | 8 seconds |
| V | 28 seconds | 36 seconds | 11 seconds | 11 seconds |
| Break Time | 1 hour[1] | 1.5 hours[1] | 2.5 hours[3] | 3.75 hours[4] |

[1]Peak to 100 cP.
[2]See Table 1; Peak to 100 cP.
[3]Last peak to 100 cP; the peak was at about 1 hour
[4]Peak to 150 cP.
[5]See Table 1

It is readily seen that Compositions 1, 3 and 4, containing a crosslinker of our invention, not only formed gels significantly more quickly than the comparative Composition 2, but the duration of the gel (break time) was significantly longer, especially with Compositions 3 and 4. Gels of our invention enable the proppant to be suspended more quickly and firmly, and provide a longer time, under the higher temperatures of the subterranean formation, for the fracturing fluid containing the proppant to be useful.

The gel results at temperatures lower than −20° C. show that our system may be used with the fracturing fluid preparation apparatus and methods described by Loree et al in U.S. patent application Ser. No. 12/203,072, also found under publication number US 2010-0051272 A1, published Mar. 4, 2010. Among other techniques described in this publication, the gel is shown being formed in the presence of or during the feeding of the proppant to a positive displacement pump.

In practical application of our invention at the wellhead, typically the phosphate gellant is added to a $C_3$-$C_5$ hydrocarbon base (frequently liquid propane or LNG, already at a temperature lower than (−)20° C.), and the gel breaker is added. The proppant, such as sand, is added as the mixture is pumped to obtain a good dispersion and our iron crosslinking agent follows within seconds. Our gel composition substantially reduces erosion of pumps and other equipment by the proppant compared to other combinations because it sets up very fast, providing substantial benefit to operators in maintenance savings.

Our invention therefore can be seen to include a method of making an iron crosslinker for use in hydrocarbon gel formation at temperatures lower than −20° C. comprising (1) forming a substantially uniform mixture of (a) ferric sulfate containing 0.8% to 1.3% by weight sulfuric acid, (b) citric acid, (c) monoisopropanolamine, and (d) ammonium hydroxide, (2) mixing sodium cumene sulfonate into the mixture and (3) slowly dissolving ferric ammonium citrate (red or brown), into the mixture under conditions effective to complete an exothermic reaction in the mixture.

Our invention also includes a method of forming an LPG hydrocarbon gel useful in formation fracturing comprising (a) injecting into an LPG base 0.5 to 5.0 weight percent based on the LPG base of an alkanol phosphate ester gel former wherein the alkanol phosphate ester comprises a diester of $C_3$, $C_4$, $C_5$, and $C_6$ alkanols or mixtures of the diesters, and (b) mixing into the LPG 0.5 to 5.0 weight percent based on the LPG of an iron crosslinker made by the method of the paragraph above.

In addition, our invention includes a composition useful for forming gels in liquified propane comprising the reaction product of, by weight, (a) 57-63.5 parts by weight ferric sulfate, (b) 4.37-4.83 parts by weight ferric ammonium citrate (brown), (c) 11.4-12.6 parts by weight citric acid, (d) 12.06-13.33 ammonium hydroxide, and (e) 10.07-11.13 monoisopropanolamine.

Also, our invention includes a low temperature hydrocarbon gel composition useful in fracturing subterranean formations comprising a (a) a liquefied alkane having 3, 4, or 5 carbon atoms or a mixture of such alkanes, (b) a phosphate ester gel former, and (c) an iron crosslinker for the phosphate ester comprising the reaction product of, by weight, (a) 57-63.5 parts by weight ferric sulfate, (b) 4.37-4.83 parts by weight ferric ammonium citrate (red or brown), (c) 11.4-12.6 parts by weight citric acid, (d) 12.06-13.33 ammonium hydroxide, and (e) 10.07-11.13 monoisopropanolamine.

Further, our invention includes a method of fracturing an underground formation through a well comprising fracturing the formation by introducing into the well under pressure sufficient to fracture the underground formation a gelled fracturing composition, at a temperature lower than (−)20° C., of a composition comprising (a) LPG, (b) a phosphate gel former, and (c) an iron crosslinker for the phosphate ester comprising the reaction product of, by weight, (i) 57-63.5 parts by weight ferric sulfate, (ii) 4.37-4.83 parts by weight ferric ammonium citrate (red or brown), (iii) 11.4-12.6 parts by weight citric acid, (iv) 12.06-13.33 ammonium hydroxide, and (v) 10.07-11.13 monoisopropanolamine.

As disclosed in this continuation-in-part application, our invention also comprises a method of making an iron crosslinker for use in hydrocarbon gel formation at temperatures lower than −20° C. comprising (1) forming a substantially uniform mixture of ingredients, in active parts by weight, comprising (a) 30 to 33.6 ferric sulfate containing 0.8% to 1.3% by weight sulfuric acid, (b) 10 to 50 citric acid, (c) 8.9 to 10 monoisopropanolamine, and (d) 3.1 to 3.6 ammonium hydroxide, (2) dissolving (e) 3.8 to 4.5 parts by weight ferric ammonium citrate (red or brown), into said mixture and (3) mixing (f) 4.25 to 4.8 parts by weight sodium cumene sulfonate into said mixture, whereby an exothermic reaction is effected in said mixture, and a composition useful for forming gels in liquified propane comprising the reaction product of, by weight, (a) 57-63.5 parts by weight ferric sulfate, (b) 4.37-4.83 parts by weight ferric ammonium citrate (red or brown), (c) 11.4-50 parts by weight citric acid, (d) 12.06-13.33 ammonium hydroxide, and (e) 10.07-11.13 monoisopropanolamine.

The invention claimed is:

1. Composition useful for forming gels in liquified propane comprising the reaction product of, by weight, (a) 57-63.5 parts by weight ferric sulfate, (b) 4.37-4.83 parts by weight ferric ammonium citrate (red or brown), (c) 11.4-50 parts by weight citric acid, (d) 12.06-13.33 ammonium hydroxide, and (e) 10.07-11.13 monoisopropanolamine.

2. Composition of claim 1 wherein said ferric sulfate includes 0.8 to 1.5 parts by weight sulfuric acid.

3. Composition useful for forming gels in liquified propane comprising the reaction product of, by weight, (a) 57-63.5 parts by weight ferric sulfate, (b) 4.37-4.83 parts by weight ferric ammonium citrate (red or brown), (c) 11.4-50 parts by weight citric acid, (d) 12.06-13.33 ammonium hydroxide, and (e) 10.07-11.13 monoisopropanolamine, said composition being substantially free of water.

4. A low temperature hydrocarbon gel composition useful in fracturing subterranean formations comprising a (a) liquefied propane, (b) a phosphate ester gel former, and (c) an iron crosslinker for the phosphate ester gel former comprising a composition of claim 1 in an amount sufficient to form a gel with said phosphate ester gel former in said liquefied propane.

5. The hydrocarbon gel composition of claim 4 including a proppant in an amount sufficient to maintain fissures in a subterranean formation.

6. The low temperature hydrocarbon gel composition of claim 4 including a hard burned magnesium oxide gel breaker in an amount sufficient to effect a delayed breaking of said gel.

7. Method of fracturing an underground formation through a well comprising fracturing said formation by introducing into said well under pressure sufficient to fracture said underground formation a gelled fracturing composition, at a temperature lower than (−)20° C., of a low temperature hydrocarbon gel composition of claim 4.

8. Method of claim 7 wherein said gelled fracturing composition includes a proppant.

9. Method of claim 7 wherein said phosphate gel former comprises a C3-C4 alkanol phosphate diester.

10. Method of claim 7 wherein said ferric sulfate includes 0.8 to 1.5 parts by weight sulfuric acid.

* * * * *